United States Patent [19]
Gill

[11] Patent Number: 5,661,534
[45] Date of Patent: Aug. 26, 1997

[54] PERIPHERAL VISION LIMITING VISOR

[76] Inventor: Michael Mintaek Gill, 3250 Wilshire Blvd. Ste. 2009, Los Angeles, Calif. 90010

[21] Appl. No.: 583,573

[22] Filed: Jan. 2, 1996

[51] Int. Cl.⁶ .................................. G02C 1/00; A61F 9/00
[52] U.S. Cl. ............................ 351/41; 2/12; 2/13
[58] Field of Search ........................ 351/44, 53, 111, 351/47, 57, 59, 158, 41; 2/12, 13

[56] References Cited

U.S. PATENT DOCUMENTS

| | | | |
|---|---|---|---|
| D. 238,831 | 2/1976 | Helfand | 2/12 |
| 4,106,119 | 8/1978 | Taupin | 351/111 |
| 4,793,006 | 12/1988 | Dawson | 2/12 |

Primary Examiner—Hung X. Dang

[57] ABSTRACT

Vision limiters including an upper sheet assembly and two side sheet assemblies to be positioned on a head for framing the vision path of an individual. A bottom sheet assembly may also be employed, thereby creating a rectangular or an oval rectangular vision path which restricts peripheral views. An extension sheet or sheets are positioned within a guideway or slot in one or more of the sheet assemblies or are slidably attached to the shield, or are pivotally mounted thereto such that extended positions as well as retracted positions may be employed to further limit peripheral view. Partial toothed surfaces provide some resistance to sliding of the sheet extensions which may be positioned in guideways or slots. A hanger system such as ear pieces and a nose piece or clips hold the device in place to frame a direct view.

22 Claims, 11 Drawing Sheets

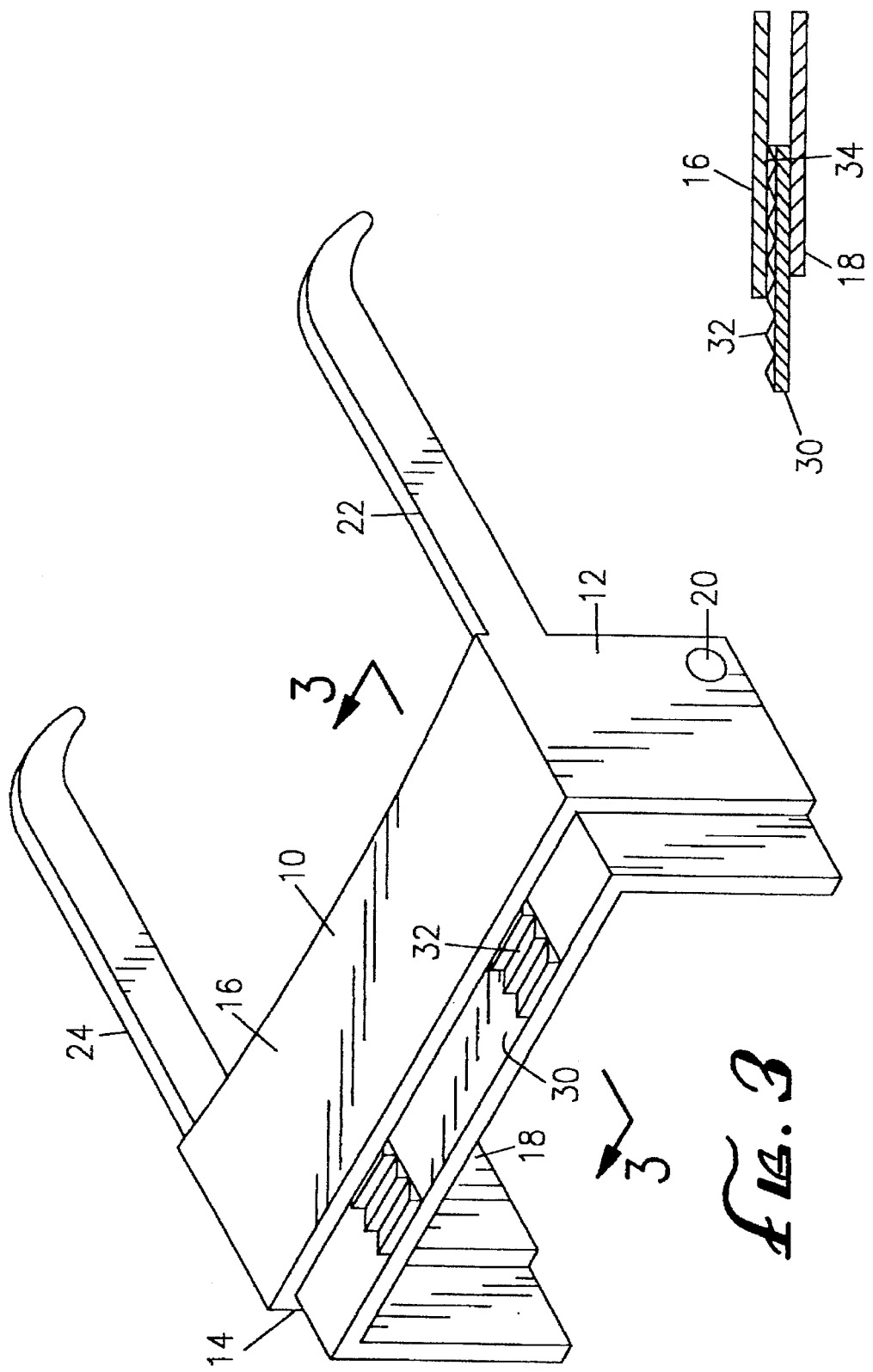

5,661,534

PERIPHERAL VISION LIMITING VISOR

BACKGROUND OF THE INVENTION

The field of the present invention is vision restricting systems for human beings.

Vision limiting systems are known for the protection of the eyes. Such devices associated with eyeglasses and head gear have been known for either shielding the eyes from damage or distraction. Such devices provide opaque or tinted sheet material affixed to a structure which can be positioned and retained on the head. In some instances, the opaque or tinted sheet material may be pivotally mounted such that it may be moved to a stowed position or into a shielding position.

SUMMARY OF THE INVENTION

The present invention is directed to a vision limiting system which eliminates peripheral vision. Shielding material is arranged such that at least the top and sides of the direct vision path of an individual wearing the present invention will be blocked from view. This allows for reading concentration and concentration while playing golf or doing other closeup detail work.

In another aspect of the present invention is that the degree of shielding is adjustable through the use of extenders. The extenders telescope outwardly from a slot or slots on the shield or are slidably attached to the shield so that they slide in and out.

In this way, the visual limitation may be moderated for reasons of safety or the like. Interlocking elements may cooperate between the assembly and the extensions to assure retention of the selected vision limitation.

In another aspect of the present invention, hinged extensions may be used where only a fully opened and fully closed position would be acceptable.

Accordingly, it is an object of the present invention to provide improved vision limiters to aid concentration. Other and further objects and advantages will appear hereinafter.

BRIEF DESCRIPTION OF THE DRAWINGS

FIG. 3 is a perspective view of the second system with a vision limiting extension deployed.

FIG. 4 is a cross-sectional view taken along line 3—3 of FIG. 3.

DETAILED DESCRIPTION OF THE PREFERRED EMBODIMENTS

Figure 1:
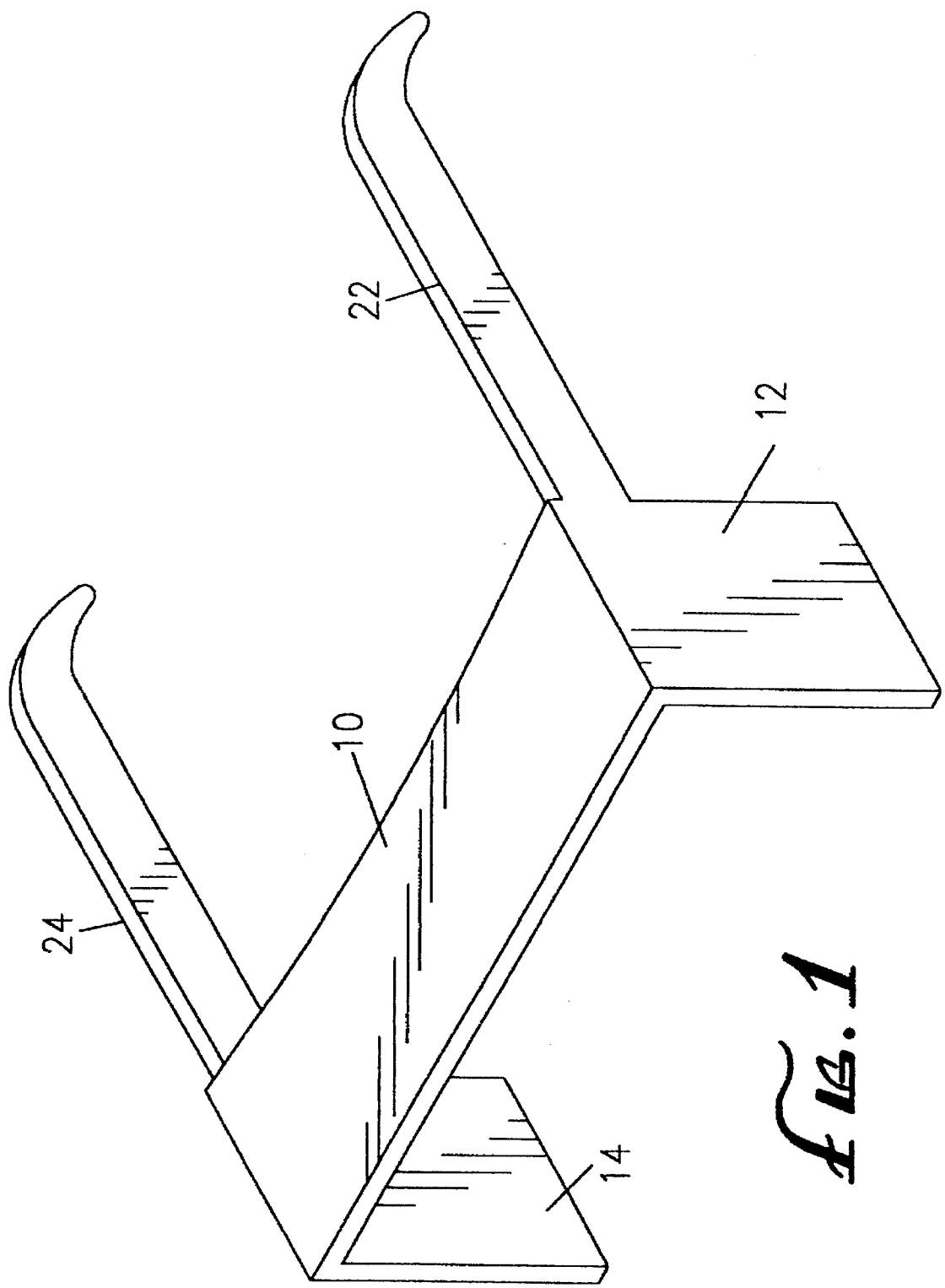
FIG. 1 is a perspective view of a first vision limiter system.

Turning in detail to the drawings, FIG. 1 illustrates a first embodiment of a vision limiter. The vision limiter includes an upper sheet assembly 10 and side sheet assemblies 12 and 14. The assemblies 10, 12 and 14 are shown to be made of the same sheet materials formed so that the side sheet assemblies 12 and 14 extend substantially perpendicularly to the upper sheet assembly 10 from either end thereof. The assemblies 10, 12 and 14 have at least one and a quarter inch width in order to limit vision sufficiently.

Associated with the sheet assemblies 10, 12 and 14 is a hanger extending from one or more of these assemblies to support the vision limiter on a human head. The hanger is configured such that the vision limiter is appropriately placed about the direct view of the individual wearing the device. A narrowed view passage is thus defined by the sheet assemblies 10, 12 and 14. In the embodiments, the hanger is shown to be ear pieces 22 and 24 which may form part of the sheet assemblies 10, 12 or 14, or may be hinged as conventional glasses. The hanger may alternatively include clips for attachment to conventional glasses much as clips are available for adding tinted lenses to conventional glasses.

Figure 2:
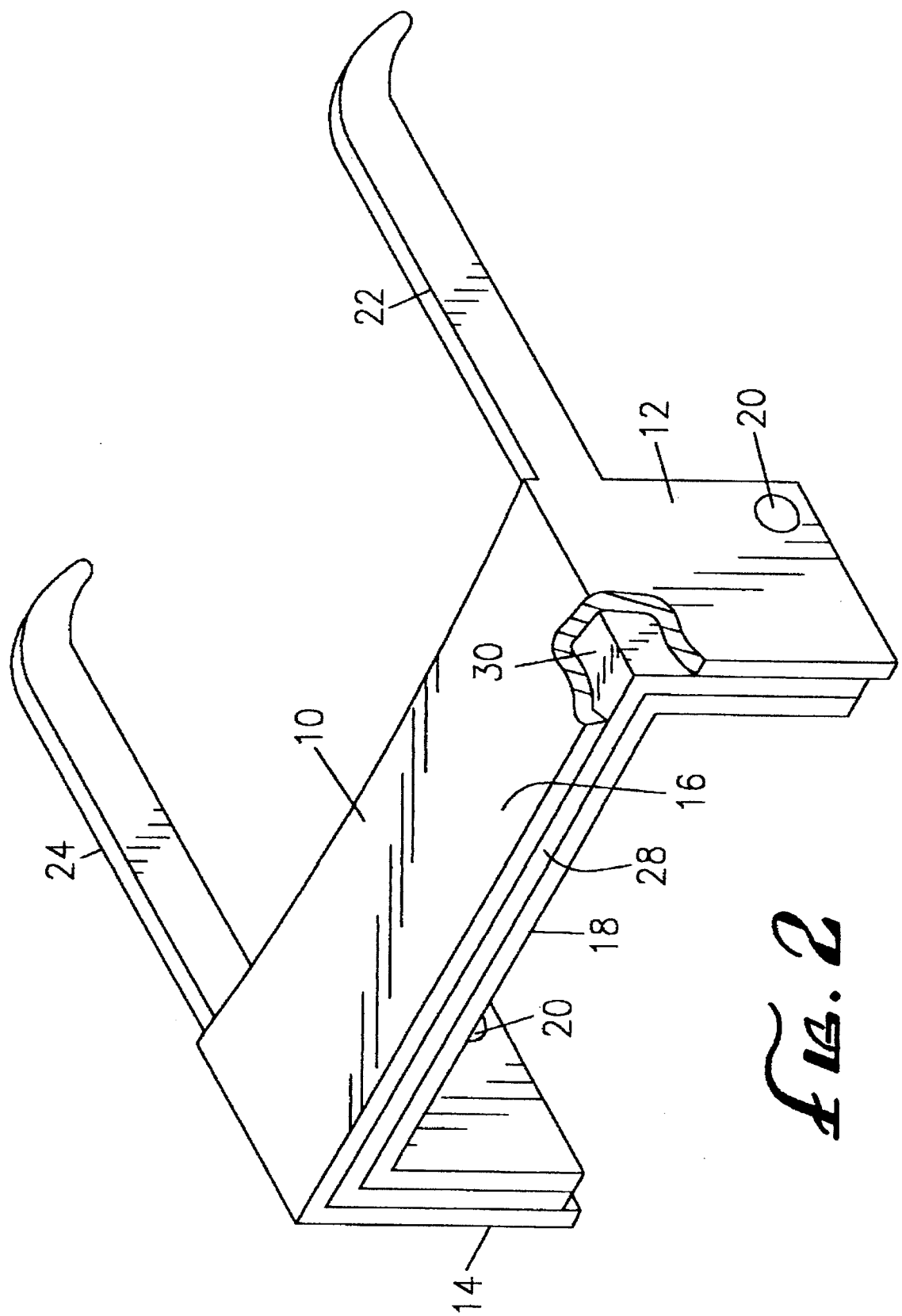
FIG. 2 is a perspective view of a second vision limiter system.

In FIG. 2, a second embodiment of a vision limiter is illustrated. The sheet assemblies 10, 12 and 14 include two juxtaposed sheets 16 and 18. The sheets 16 and 18 are affixed together at one or more points along the periphery. Fasteners are illustrated as one example.

Figure 5:
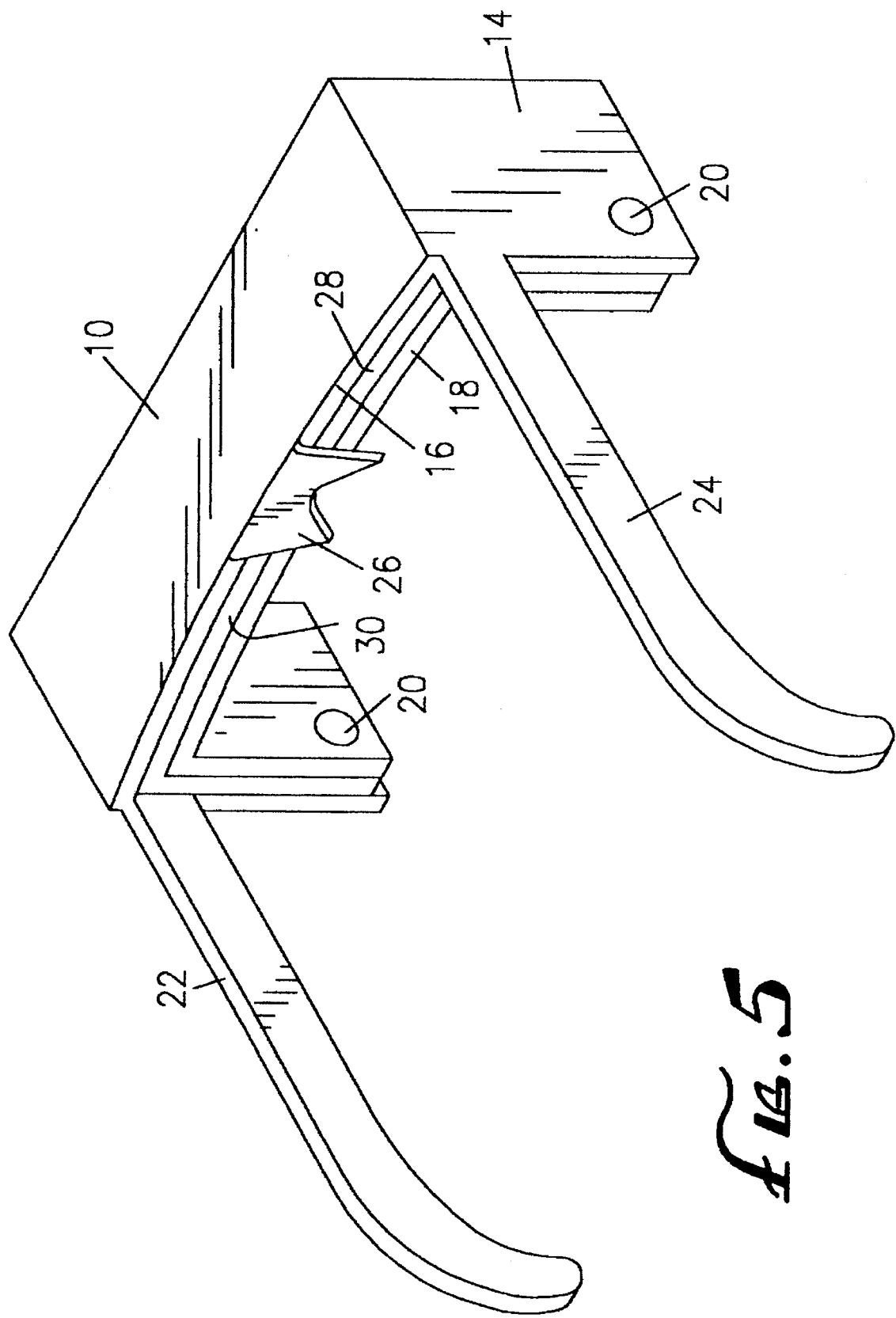
FIG. 5 is a perspective view of the system of FIG. 2 illustrating the back side thereof.

FIG. 5 illustrates a nose bridge piece 26 which cooperates with the ear pieces 22 and 24.

The sheets 16 and 18, fastened as they are at the back periphery by the fasteners 20, define a guideway 28 which extends fully across the upper sheet assembly 10 and down each side sheet assembly 12 and 14. Positioned within the guideway 28 is a sheet extension 30. The sheet extension 30 includes a fully retracted position which may be substantially out of sight as seen in FIG. 2, a fully extended position as illustrated in FIG. 3 and of course any position in between. As with the sheets 16 and 18, the sheet extension 30 is shown to be all one piece with an upper sheet extension and side sheet extensions defined by the formation of the sheet. Alternatively, the sheet extension 30 may be broken into three sheets, separate upper and side extensions, for greater flexibility of adjustment.

As illustrated in FIGS. 3 and 4, the upper surface of the sheet extension 30 includes a partially toothed surface 32 which is shown to be in two strips. A corresponding surface 34 defines a partial toothed surface on the inner side of the sheet 16 so as to cooperate with the toothed surface 32. The materials are sufficiently flexible such that the extension may be moved inwardly and outwardly without difficulty.

The device of FIGS. 2 through 5 can be used when an individual would like greater concentration or the avoidance of bright lights or the like. The degree to which limitation on peripheral vision is desired may be accommodated by the sheet extension 30.

Figure 6:
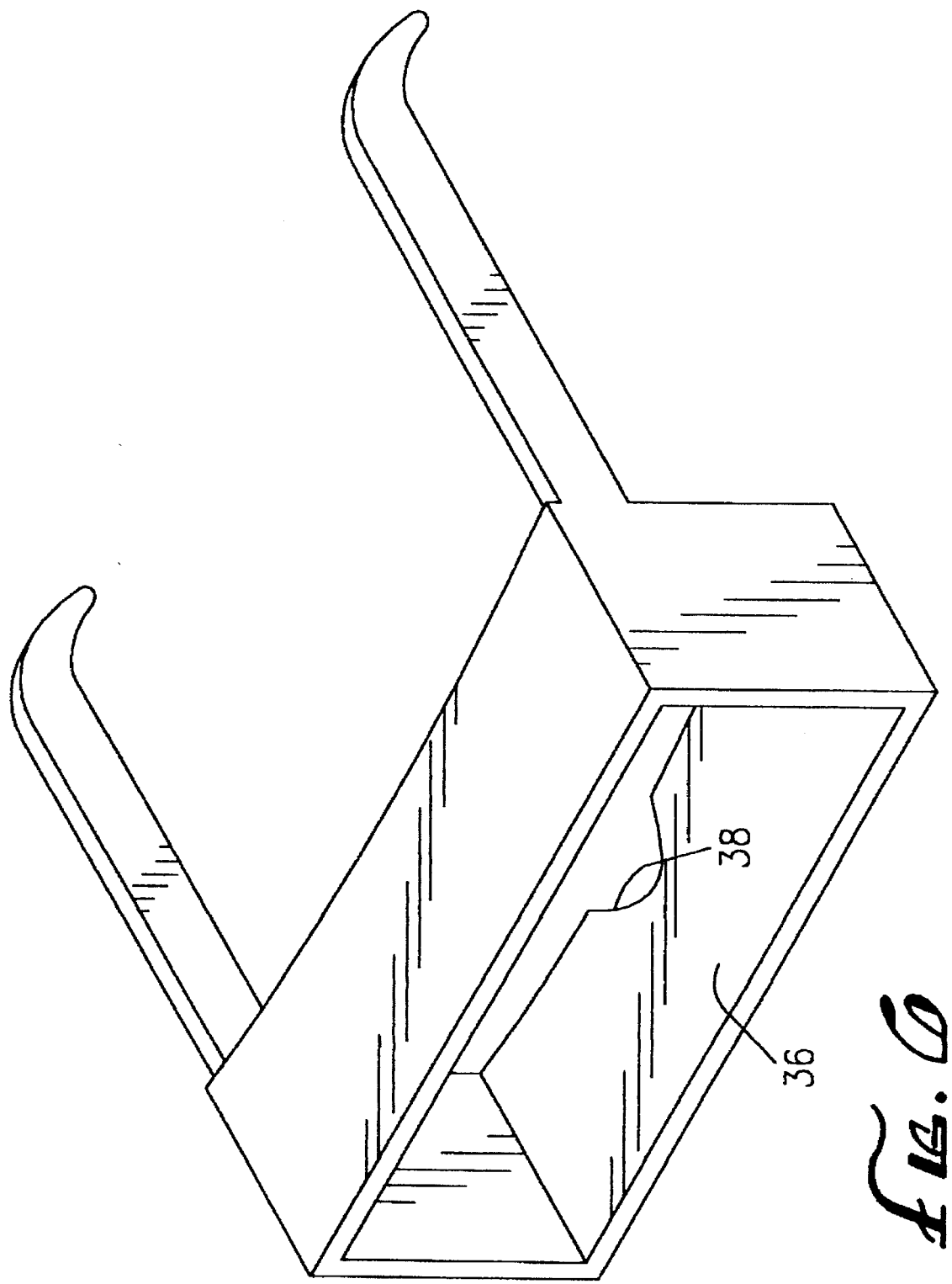
FIG. 6 is a perspective view of a third vision limiter system.
Figure 7:
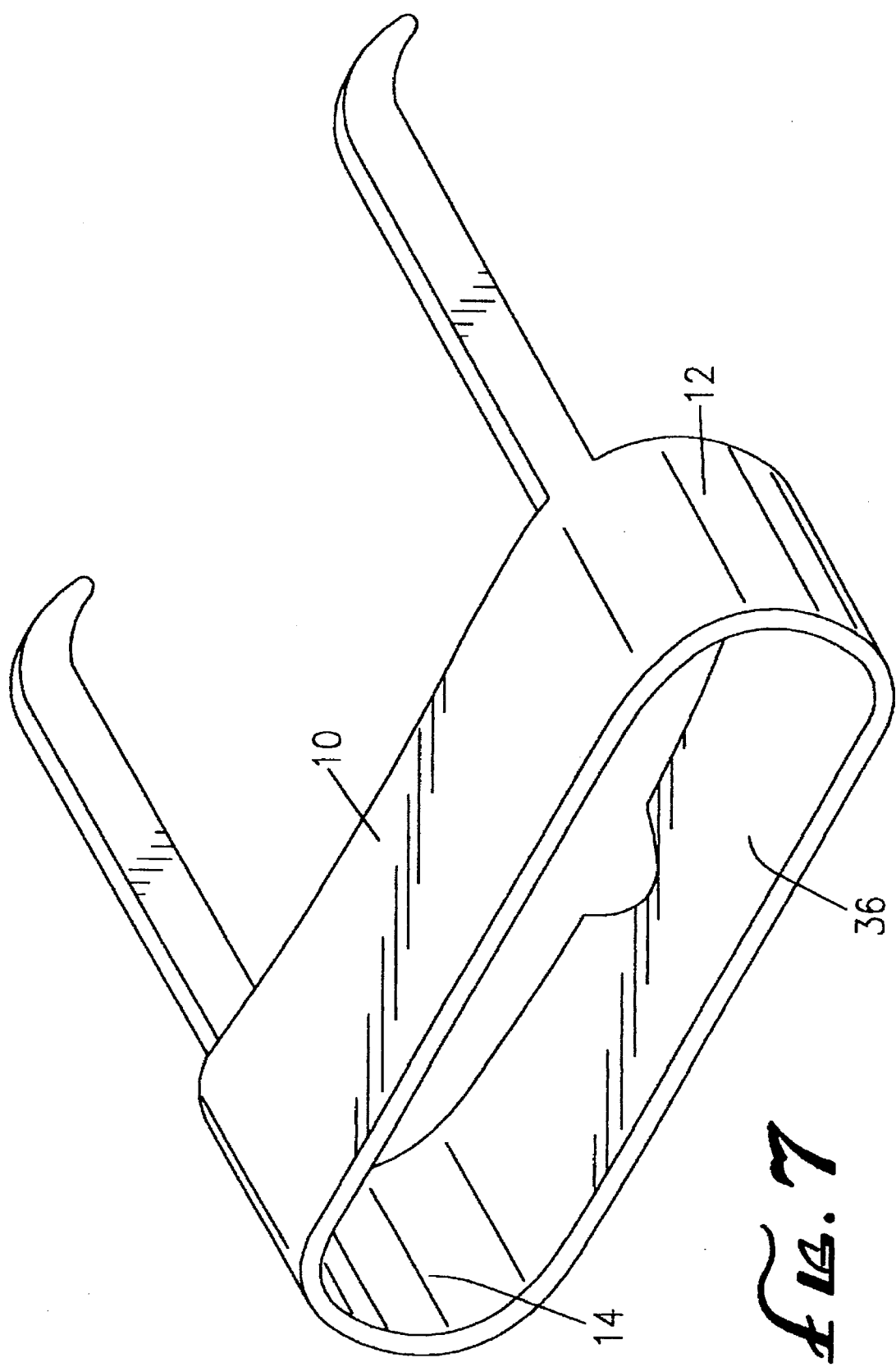
FIG. 7 is a perspective view of a third vision limiter system with concave side sheets.

Turning next to FIG. 6, a third embodiment is illustrated which uses similar numbers for similar elements as employed with FIGS. 1 through 5. In the embodiment of FIG. 6, a lower sheet 36 is added to the first embodiment which is shown in FIG. 1. The lower sheet 36 is employed for strength as well as a further vision limiter. The sheet 36 may also have a concave edge 38 for receiving the nose of the wearer. FIG. 7 illustrates vision limiter same as one shown in FIG. 6 except shape of side sheet assemblies 12 and 14. The vision limiter in FIG. 7 has concave shaped side sheet assemblies 12 and 14 so that the vision limiter would have an oval shape rectangle when viewed from the front.

Figure 8:
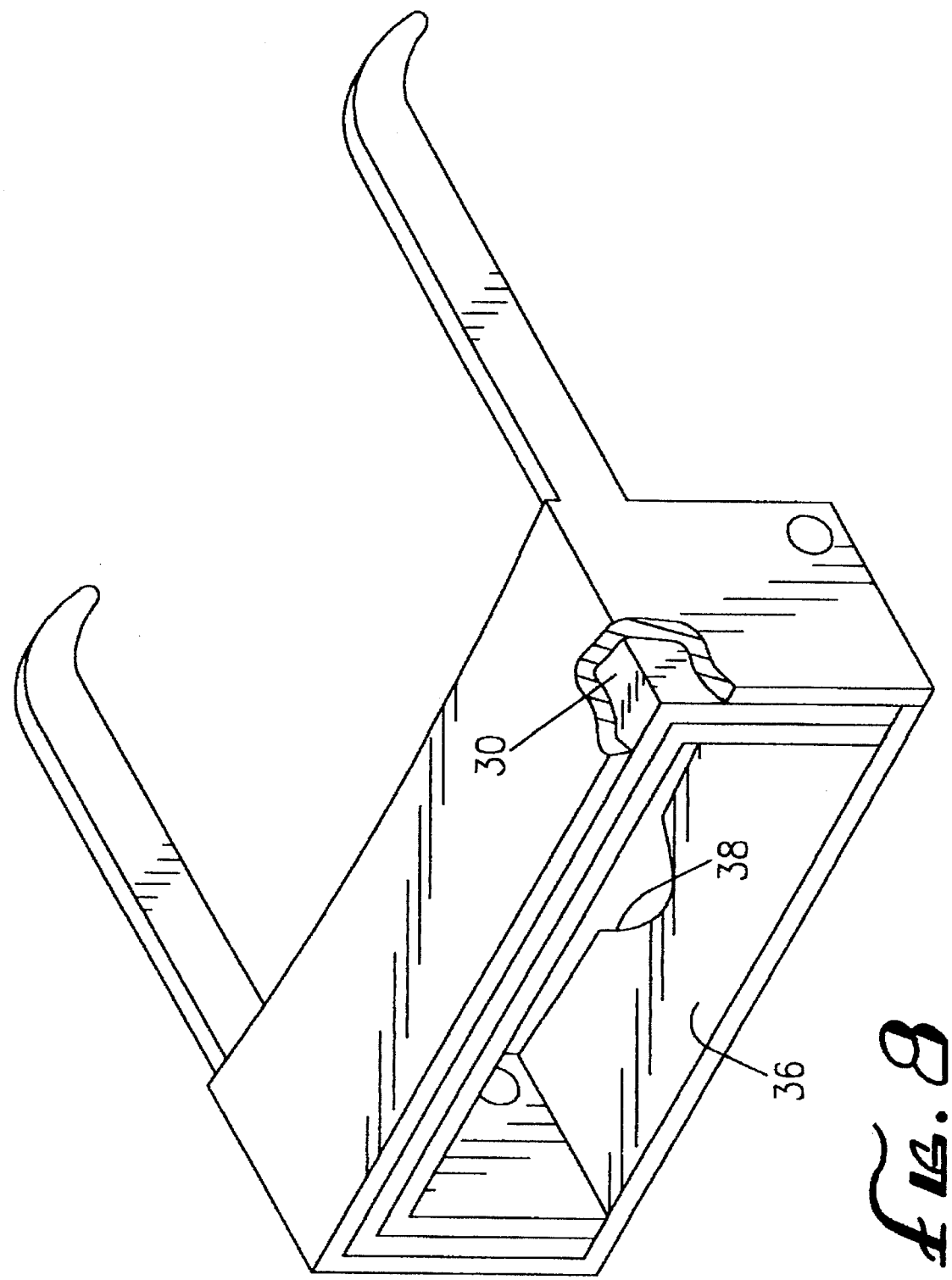
FIG. 8 is a perspective view of fourth vision limiter system.
Figure 9:
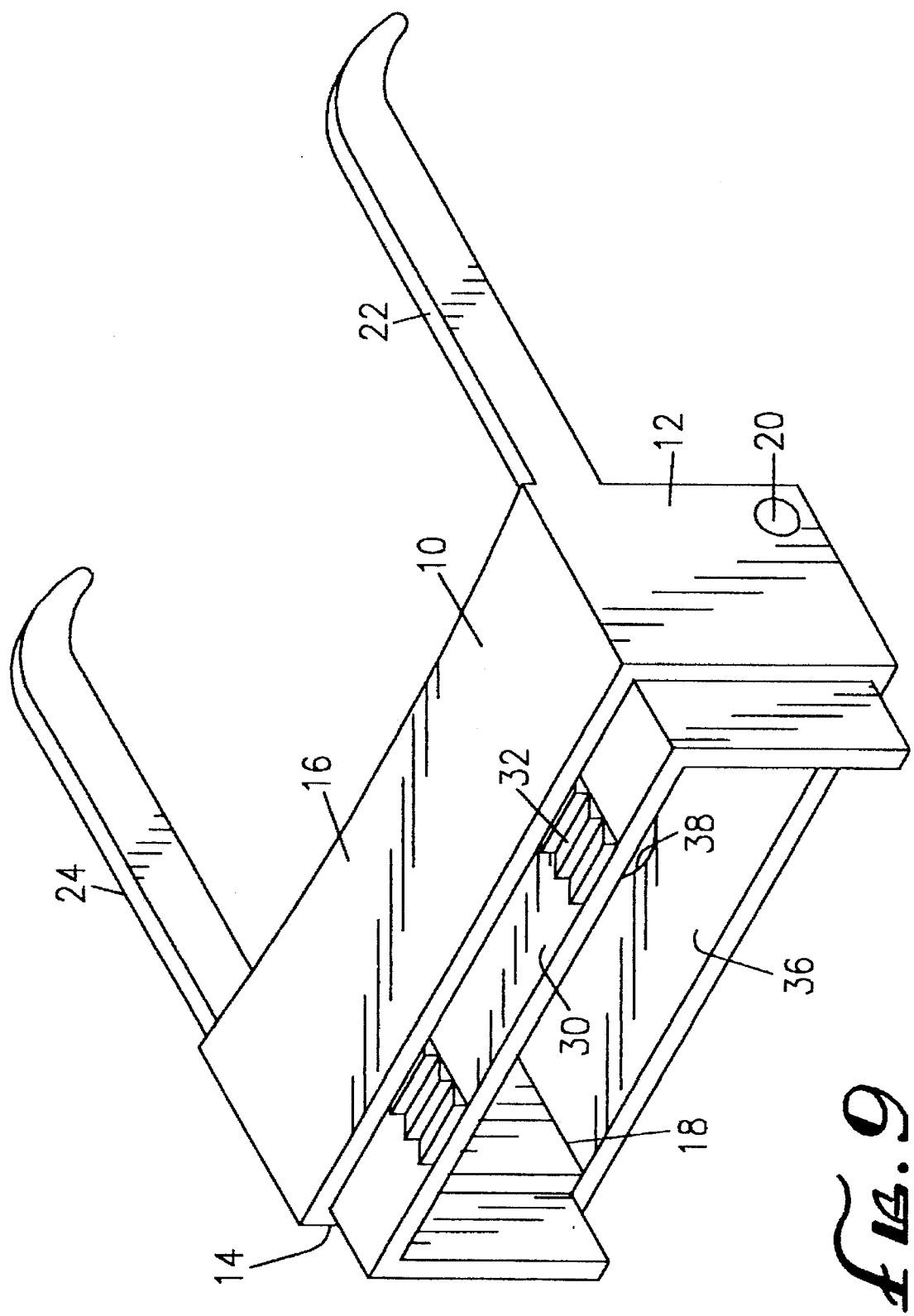
FIG. 9 is a perspective view of the system of FIG. 8 with the vision limiting extension deployed.

Turning next to FIG. 8, lower sheet 36 is added to the vision limiter shown in FIG. 2. FIG. 9 illustrates the device of FIG. 8 with the sheet extension 30 extending outwardly toward its most extended position.

Figure 10:
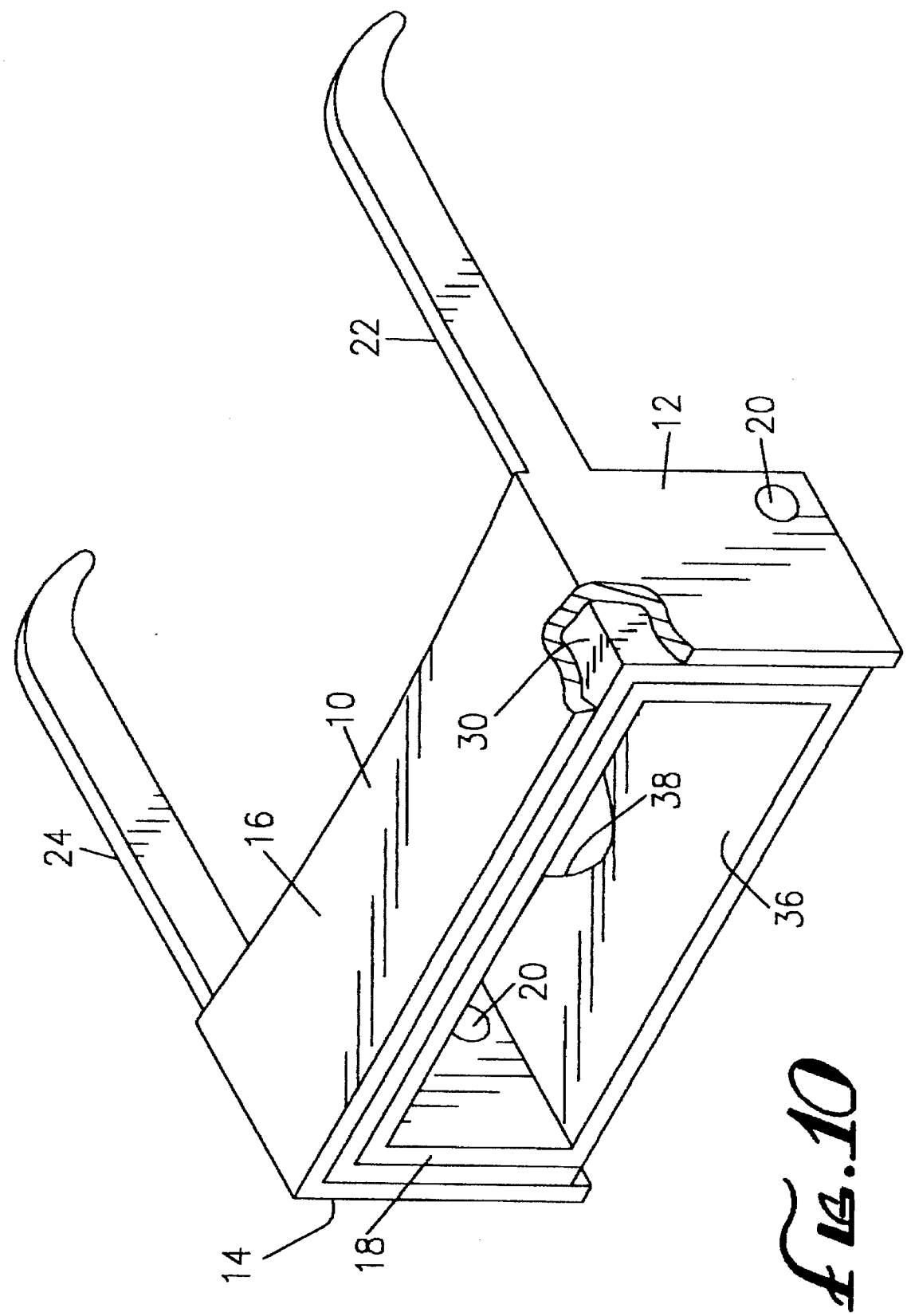
FIG. 10 is a perspective view of yet another vision limiter system.
Figure 11:
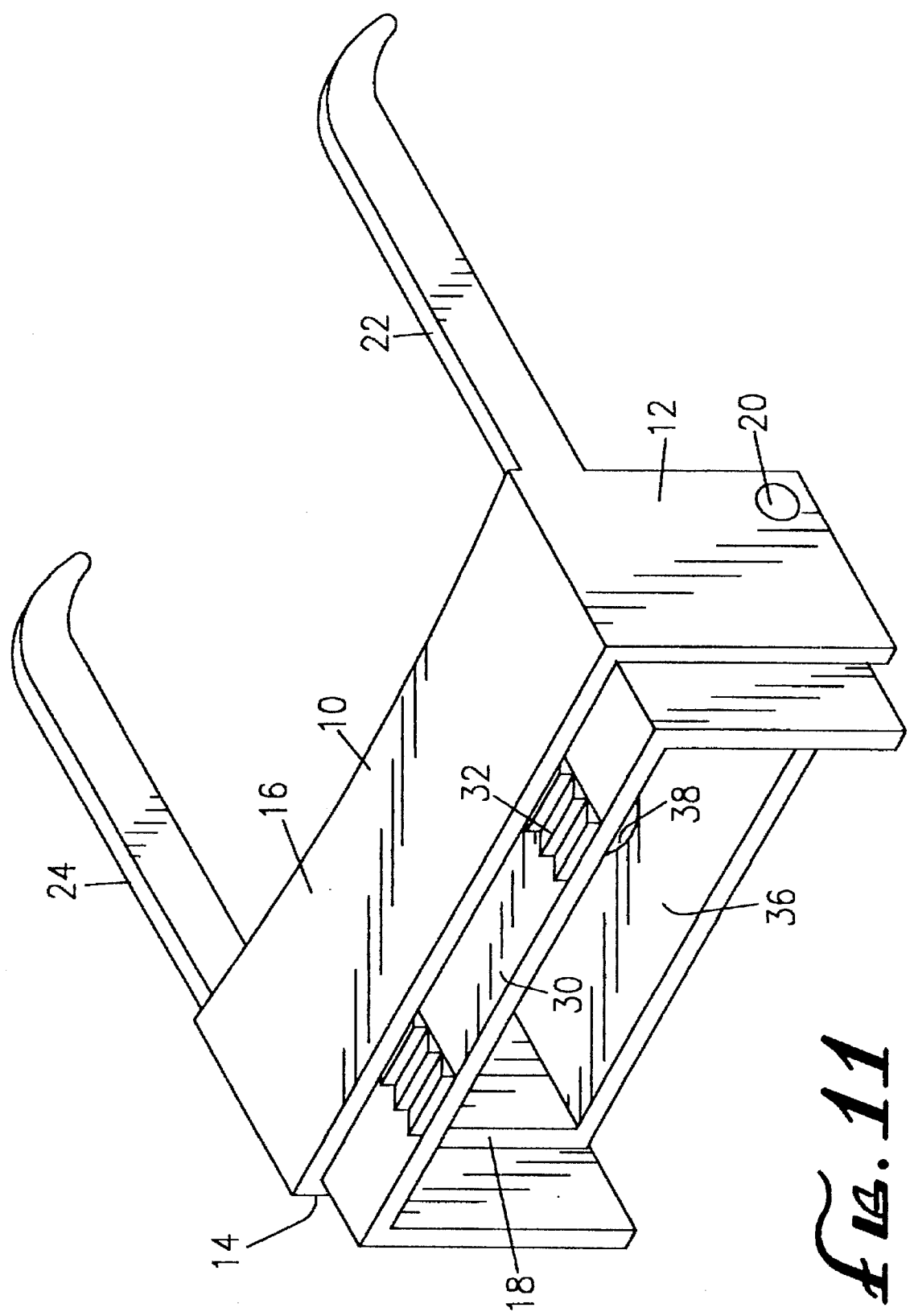
FIG. 11 is a perspective view of the system of FIG. 10 with the vision limiting extension deployed.

FIGS. 10 and 11 provide yet another configuration illustrating that the inner sheet 18 may provide the lower sheet 36 with the concave edge 38.

Figure 12:
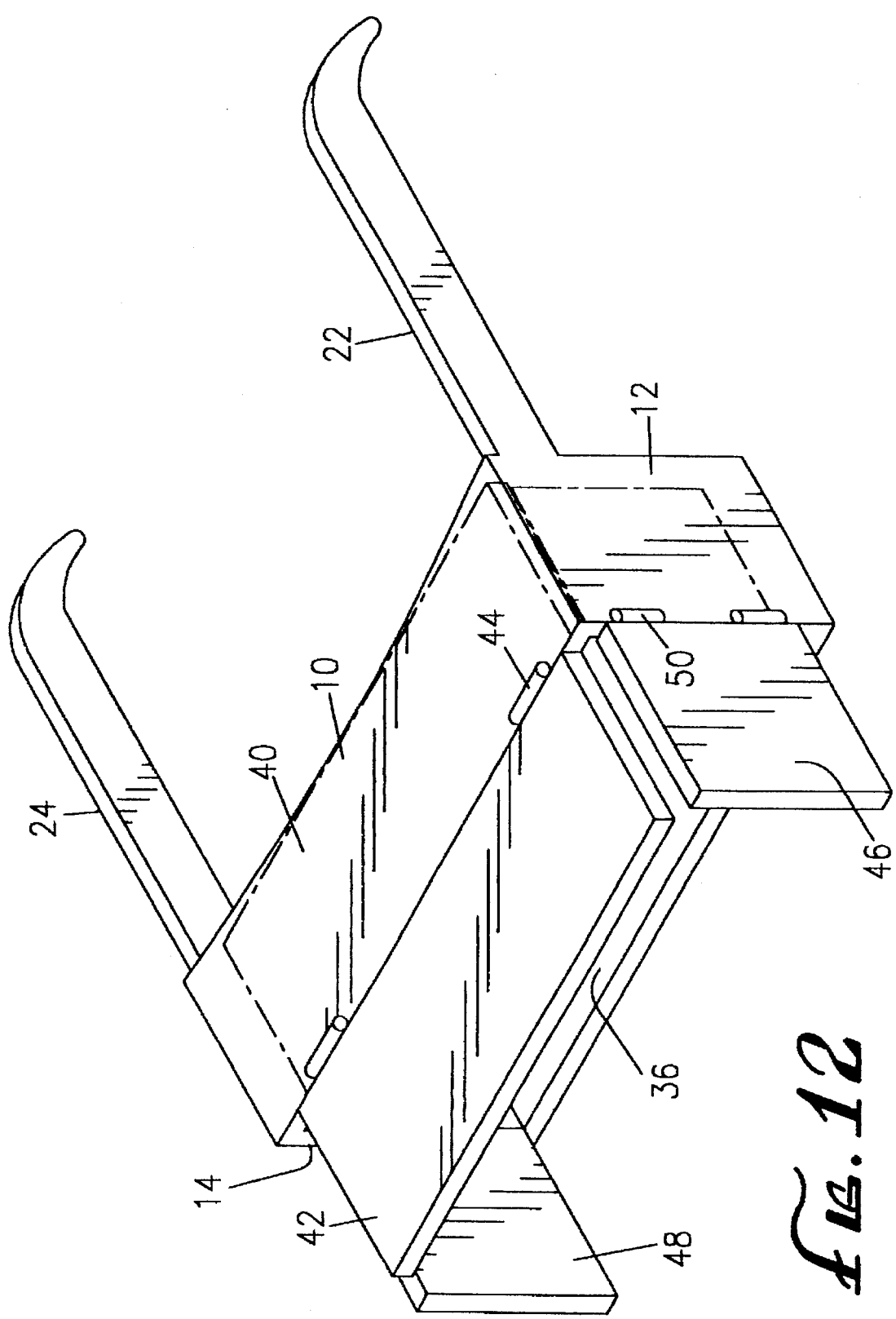
FIG. 12 is a perspective view of yet another vision limiter system with vision limiting extensions deployed.

Turning to FIG. 12, a single sheet 40 defines the side assemblies 12 and 14 as well as the upper sheet assembly 10 and the lower sheet assembly 36. To provide sheet extensions, an upper sheet extension 42 is hinged by hinges 44 to the upper sheet assembly 10. The hinges 44 allow the sheet 42 to assume a fully extended position as well as a fully retracted position as illustrated in phantom. Side sheet extensions 46 and 48 employ hinges 50 to operate in the same manner.

Substantially any of the foregoing features described may be employed in combination with one another as illustrated in the several embodiments. For example, the outer sheet 16 and inner sheet 18 might both extend fully in a rectangle with a guideway or slot provided on all four sides for a sheet extension 30 or several separate sheet extensions for each side. In addition, the device, shown to be fabricated of sheet materials such as plastic or paper may be molded or otherwise formed. The material may be opaque or any degree of translucence.

Thus, a useful device for limiting vision to be worn independently of or in conjunction with eyeglasses is disclosed. While embodiments and applications of this invention have been shown and described, it would be apparent to those skilled in the art that many more modifications are possible without departing from the inventive concepts herein. The invention, therefore is not to be restricted except in the spirit of the appended claims.

What is claimed is:

1. A vision limiter for human eyes, comprising
   an upper sheet assembly having first and second upper ends;
   two side sheet assemblies extending substantially perpendicular to the upper sheet assembly, one side sheet assembly extending from the first upper end and the other side sheet assembly extending from the second upper end, the upper sheet assembly and the two side sheet assemblies defining a view passage there among;
   a hanger extending from one or more of the upper sheet assembly and the two side sheet assemblies to support the upper and the two side sheet assemblies with the view passage in front of the human eyes;
   an upper sheet extension having a retracted position juxtaposed with the upper sheet assembly, and having an extended position extending outwardly from and in substantially coplaner relation with the upper sheet assembly;
   side sheet extensions each having a side retracted position juxtaposed with the side sheet assemblies, respectively, and an extended position extending outwardly from and in coplaner relation with the side sheet assemblies, respectively, the side sheet extensions and the upper sheet extension being one piece.

2. The vision limiter of claim 1, the hanger including ear pieces extending from the two side sheet assemblies and a nose bridge piece centrally of the upper sheet assembly to rest on the nose between the human eyes.

3. The vision limiter of claim 1, the upper sheet assembly including a guideway, the upper sheet extension being slidable positioned in the guideway.

4. The vision limiter of claim 3, the guideway being a slot extending substantially the width of and set within the upper sheet assembly.

5. The vision limiter of claim 1 further comprising a lower sheet assembly extending substantially parallel to and displaced laterally from the upper sheet assembly and having first and second lower ends attached to the side sheet assemblies, the lower sheet assembly further defining the view passage.

6. The vision limiter of claim 5, the lower sheet assembly further having a concave edge portion centrally of the lower sheet to rest on the nose between the human eyes.

7. The vision limiter of claim 5, the view passage being rectangular with the upper and lower sheets being closer together than the two side sheets.

8. The vision limiter of claim 5, the view passage being oval shaped rectangular with the upper and lower sheets being close together than the two side sheets, and the two side sheet assemblies having concave shape curving outward.

9. The vision limiter of claim 5, the hanger including ear pieces extending from the two side sheets and a nose bridge piece centrally of the upper sheet to rest on the nose between the human eyes.

10. The vision limiter of claim 5 further comprising a central sheet extending between the center of the upper sheet to the center of the lower sheet and substantially parallel to the side sheets.

11. The vision limiter of claim 5 further comprising hinges pivotally mounting the upper sheet extension to the distal edge of the upper sheet assembly and the two side sheet extensions to the distal edges of the side sheet assemblies, respectively.

12. A vision limiter for human eyes, comprising
    an upper sheet assembly having at least one and a quarter inch width and having first and second upper ends;
    two side sheet assemblies extending substantially perpendicular to the upper sheet assembly, one side sheet assembly extending from the first upper end and the other side sheet assembly extending from the second upper end, the upper sheet assembly and the two side sheet assemblies defining a view passage thereamong;
    a hanger extending from one or more of the upper sheet assembly and the two side sheet assemblies to support the upper and the two side sheet assemblies with the view passage in front of the human eyes;
    an upper sheet extension having a retracted position juxtaposed with the upper sheet assembly, and having an extended position extending outwardly from and in substantially coplaner relation with the upper sheet assembly, the upper sheet assembly including a guideway, the upper sheet extension being slidably positioned in the guideway, the guideway being a slot extending substantially the width of and set within the upper sheet assembly, the upper sheet extension having a first partial toothed surface and the guideway having a second partial toothed surface mating with the first partial toothed surface to resist sliding within the slot.

13. The vision limiter of claim 12, the upper sheet assembly including a first sheet and a second sheet juxtaposed with the first sheet and fixed to the first sheet only at a portion of the periphery of the first sheet, defining a slot between the first and second sheets, the upper sheet extension having first and second upper sheet extension ends and being slidable positioned in the slot.

14. The vision limiter of claim 13 further comprising side sheet extensions each having a side retracted position juxtaposed with the side sheet assemblies, respectively, and an extended position extending outwardly from and in coplanar relation with the side sheet assemblies, respectively, the side sheet extensions being fixed to the upper sheet extension ends.

15. The vision limiter of claim 12 further comprising a lower sheet assembly extending substantially parallel to and displaced laterally from the upper sheet assembly and having first and second lower ends attached to the side sheet assemblies, the lower sheet assembly further defining the view passage.

16. The vision limiter of claim 15, the hanger including ear pieces extending from the two side sheets and a nose bridge piece centrally of the upper sheet to rest on the nose between the human eyes.

17. The vision limiter of claim 15, the lower sheet further having a concave edge portion centrally of the lower sheet to rest on the nose between the human eyes.

18. The vision limiter of claim 17, the view passage being rectangular with the upper and lower sheets being closer together than the two side sheet assemblies.

19. The vision limiter of claim 17, the view passage being oval shaped rectangular with the upper and lower sheets being close together than the two side sheets, and the two side sheet assemblies having concave shape curving outward.

20. The vision limiter of claim 15 further comprising side sheet extension each having a side retracted position juxtaposed with the side sheet assemblies, respectively, and an extended position extending outwardly from and in coplanar relation with the side sheet assemblies, respectively.

21. The vision limiter of claim 20, the side sheet extensions and the upper sheet extension being one piece.

22. A vision limiter for human eyes, comprising
an upper sheet assembly having first and second upper ends;
two side sheet assemblies extending substantially perpendicular to the upper sheet assembly, one side sheet assembly extending from the first upper end and the other side sheet assembly extending from the second upper end, the upper sheet assembly and the two side sheet assemblies defining a view passage thereamong;
a hanger extending from one or more of the upper sheet assembly and the two side sheet assemblies to support the upper and the two side sheet assemblies with the view passage In front of the human eyes;
an upper sheet extension having a retracted position juxtaposed with the upper sheet assembly, and having an extended position extending outwardly from and in substantially coplaner relation with the upper sheet assembly, the upper sheet assembly including a guideway, the upper sheet extension being slidably positioned in the guideway, the guideway being a slot extending substantially the width of and set within the upper sheet assembly, the upper sheet extension having a first partial toothed surface and the guideway having a second partial toothed surface mating with the first partial toothed surface to resist sliding within the slot.

\* \* \* \* \*